(12) United States Patent
Jhao et al.

(10) Patent No.: US 10,646,195 B2
(45) Date of Patent: May 12, 2020

(54) TEST PHANTOM FOR X-RAY IMAGING

(71) Applicant: NATIONAL YANG MING UNIVERSITY, Taipei (TW)

(72) Inventors: Suei-Ting Jhao, Taipei (TW);
Jyh-Cheng Chen, Taipei (TW);
Wei-Hung Shih, Kaohsiung (TW);
Yu-Jie Lan, Kaohsiung (TW)

(73) Assignee: National Yang-Ming University, Taipei (TW)

( * ) Notice: Subject to any disclaimer, the term of this patent is extended or adjusted under 35 U.S.C. 154(b) by 171 days.

(21) Appl. No.: 15/862,264

(22) Filed: Jan. 4, 2018

(65) Prior Publication Data

US 2019/0110771 A1 Apr. 18, 2019

(30) Foreign Application Priority Data

Oct. 13, 2017 (TW) .............................. 106135184 A

(51) Int. Cl.
*A61B 6/00* (2006.01)

(52) U.S. Cl.
CPC ................ *A61B 6/583* (2013.01); *A61B 6/44* (2013.01)

(58) Field of Classification Search
CPC .. A61B 6/00; A61B 6/44; A61B 6/583; A61B 6/58; A61B 6/582; A61B 6/585; A61B 6/588
USPC ......................................................... 378/207
See application file for complete search history.

(56) References Cited

U.S. PATENT DOCUMENTS

| | | | |
|---|---|---|---|
| 6,231,231 B1 * | 5/2001 | Farrokhnia | A61B 6/583 378/204 |
| 10,395,560 B2 * | 8/2019 | Groenewald | G09B 23/286 |

* cited by examiner

*Primary Examiner* — Jurie Yun
(74) *Attorney, Agent, or Firm* — Muncy, Geissler, Olds & Lowe, P.C.

(57) ABSTRACT

The present invention provides a test phantom for X-ray imaging, which comprises a prosthetic fin and an edge patch; wherein the prosthetic fin has a plurality of different arithmetical series sizes of circular grooves and plurality of different arithmetical series thickness of the line pairs; wherein the edge patch connects on one side of the prosthetic fin. The present invention further provides a test phantom combination for X-ray imaging and a method for measuring parameters and focal spot.

15 Claims, 14 Drawing Sheets

TEST PHANTOM FOR X-RAY IMAGING

CROSS-REFERENCE TO RELATED APPLICATIONS

This Non-provisional application claims priority under 35 U.S.C. § 119 on Patent Application No(s). TW106135184 filed in Taiwan, Republic of China, Oct, 13, 2017, the entire contents of which are hereby incorporated by reference.

BACKGROUND OF INVENTION

Field of the Invention

This invention relates to a test phantom, which is used for testing the quality parameters of X-ray system, characterized by that a group comprises of a phantom fin and an edge plate. Wherein, there is a plurality of circular grooves with diameters and a plurality of line pairs with widths arranged in parallel on the phantom fin.

Description of Related Art

In the medical imaging diagnosis and treatment market, X-ray-related industries and technical development account for a large part, therefore the technology has developed to be specialized. In addition to the X-ray imaging equipment used in hospitals, dental clinics also need to operate X-ray imaging equipment, and the mobile X-ray mammography vehicle has gotten more and more popular. The precision requirement of modern medicine for image has become higher. According to statistics, the market of medical imaging instruments and equipment reached USD20.2 billion in 2013. It is on the continual increase. In 2017, it will be USD29.8 billion, wherein 40% is taken up by X-ray-related industries, the technologies will derive high economic value.

Currently, in medical imaging instruments use for maintaining the accuracy and precision of images, all of monitoring devices, including X-ray, CT and MRI, are in need to be periodically tested and kept in repair; In addition to that, the instruments required for measuring different parameters may not be same, it should replace the suit phantom for each correction, for example, to obtain the focal spot value by selecting a stellated phantom, it not only waste time in correction operation, but also be difficult to show the state relationship between different phantoms. Therefore, for the users of medical imaging instruments, a design of test phantom for the measurement of multiple standard parameters is required in current art.

BRIEF SUMMARY OF THE INVENTION

In view of this, the present invention provides a test phantom for X-ray imaging, which comprises a phantom fin and an edge plate that is attached to one side of the phantom fin. It has a plurality of different arithmetical series sizes of circular grooves and a plurality of different arithmetical series thickness of the line pairs.

It is preferred that these circular grooves have a diameter of 0.5 mm~4 mm respectively. In an embodiment, the diameters are 0.5, 1, 1.5, 2, 2.5, 3 and 4 mm respectively.

It is preferred that these pair lines have a width of 1 1p/mm ~10 1p/mm respectively. In an embodiment, the widths are 1, 2, 3, 4, 5, 8, 10 1p/mm respectively.

The test phantom of the present invention can comprise of a plurality of phantom fins and an edge plate. Specifically, the phantom fins have different thicknesses.

It is preferred that the phantom fins are 0.16 mm~4.63 mm wide. In an embodiment, the widths are 0.16, 0.44, 0.79, 1.07, 1.42, 2.14, 3.56 and 4.63 mm respectively.

It is preferred that the phantom fin and edge plate of test phantom in the present invention are made of tungsten, aluminum or PMMA.

In addition, the present invention provides a test phantom set used for X-ray imaging, which structurally comprises a plurality of said test phantoms. Specifically, these test phantoms have a plurality of phantom fins and an edge plate, which, moreover, is used as an identity coordinate in the shape.

In an embodiment, the test phantom set in the present invention also comprises a slot body and a stellated phantom to be placed. Specifically, the slot has a circle hollow groove, which fits the stellated phantom.

It is preferred that the diameter of the circular hollow groove is about 50 mm to 55 mm.

It is preferred that the slot in the test phantom set in the present invention is made of tungsten, aluminum or PMMA.

The present invention further provides a measurement method for the parameters of test phantom for X-ray imaging, and its steps include: (a) provide an X-ray imaging device comprising an X-ray source and an image detector; (b) place a test phantom set in the front side of the image detector; (c) shut a ray from the X-ray source passing through the test phantom set, then received by the image detector to record and obtain an image; (d) from the image, select one round slot with a limitation distinguishing degree or one line pair with a limitation contrast ratio of the test phantom set; and (e) take the value corresponding to the round slot or the line pair as the maximum resolution of the X-ray imaging device.

The steps of said measurement method further include: (f) from the image, select one edge plate of the test phantom set to obtain an edge spread function (ESF); (g) calculate the differential of the ESF to obtain a line spread function (LSF); (h) calculate the Fourier transformation of the linear spread function to obtain a modulation transfer function (MTF) (i) calculate the MTF based on a standard criterion to obtain an input power ($W_{in}$) and an output power ($W_{out}$); and (g) calculate the MTF, output power and input power to obtain a detective quantum efficiency (DQE).

The present invention provides a measurement method for the focal spot of test phantom for X-ray imaging, and its steps include: (a) provide an X-ray imaging device comprising an X-ray source and an image detector; (b) place a test phantom set with a stellated phantom between the X-ray source and the image detector, wherein the X-ray source distances the test phantoms set, and the image detector with a distance ratio; (c) shut a ray from the X-ray source passing through a stellated phantom of the test phantoms set, then received by the image detector to record and obtain an image; (d) from the image, select one region with a limitation distinguishing degree or a limitation contrast ratio of the stellated phantom; and (e) calculate the diameter and angle value of the region and the distance ratio to obtain a focal spot size or a focal spot value.

By the implementation of the present invention, technicians can easily complete the correction of X-ray imaging, without repetitively using different phantoms. In addition, the resolution ratio of the image of the round slot or line pair device can be intuitively judged, the contrast ratio of image of device can be obtained through the masking of phantom fins with different thicknesses.

Furthermore, its numerical calculation can provide such analyses on spatial resolution, contrast ratio, modulation transfer function (MTF), noise power spectrum (NPS), detective quantum efficiency (DQE), etc., or the measurement of focal value can be obtained in combination with the stellated phantom.

DETAILED DESCRIPTION OF THE INVENTION

The present invention provides a test phantom for X-ray imaging, which can be used to measure the quality of X-ray system, and measure the spatial resolution, resulting in MTF, NPS, DQE, dynamic scope of X-ray system, etc., and with the stellated phantom mounted, additionally measure focal spot, extreme resolution and defocusing value.

Figure 1:
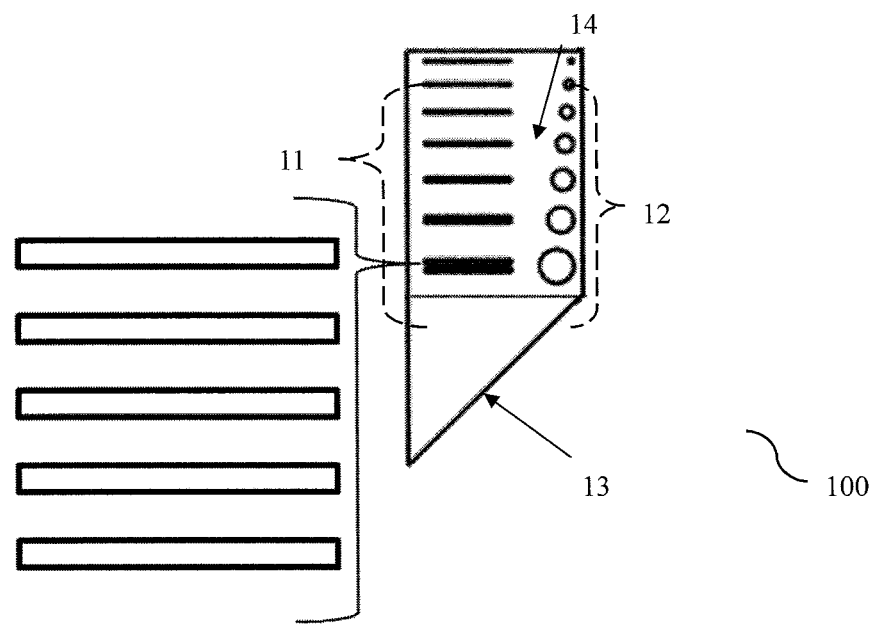
FIG. 1 is the structural diagram of test phantom of the present invention.

As shown in FIG. 1, the present invention provides a test phantom 100 comprising of a phantom fin 14 and an edge plate 13 that is attached to one side of said phantom fin. Specifically, circular grooves 12 with a plurality of diameters and line pairs 11 with a plurality of widths are arranged in parallel on the phantom fin. The line pairs respectively represent the corresponding resolution values at different spatial frequencies, and the circular grooves respectively stand for the corresponding values of different spatial resolutions. Thus, the line pairs and circular grooves can be used in clinical macroscopic reading for judgment.

Figure 2:
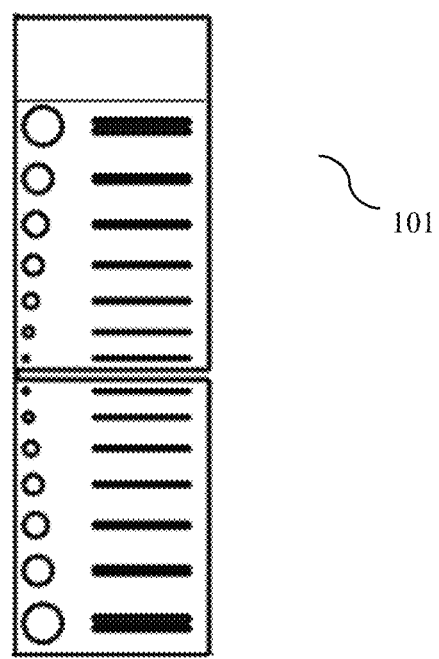
FIG. 2 is the structural diagram of the test phantom set of the present invention.

As shown in FIG. 2, a test phantom set 101 in the present invention comprises of a plurality of phantom fins 14 and an edge plate 13. Specifically, there are circular grooves 12 with a plurality of diameters and line pairs 11 with a plurality of widths on the phantom fins 14, and the phantom fins 13 in plural number have different thicknesses.

Figure 3A:
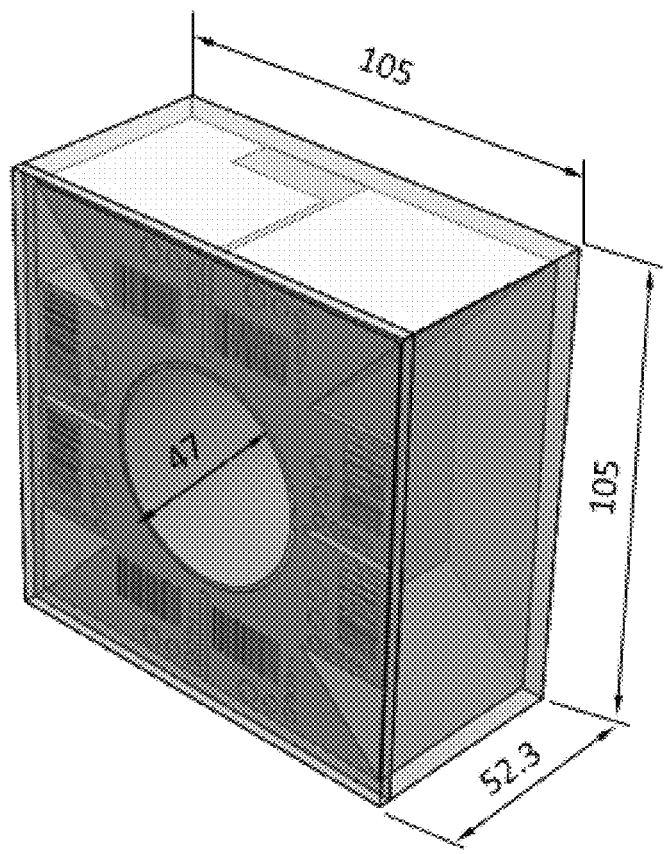
FIG. 3A is the front stereogram of the embodiment of the test phantom set of the case.
Figure 3B:
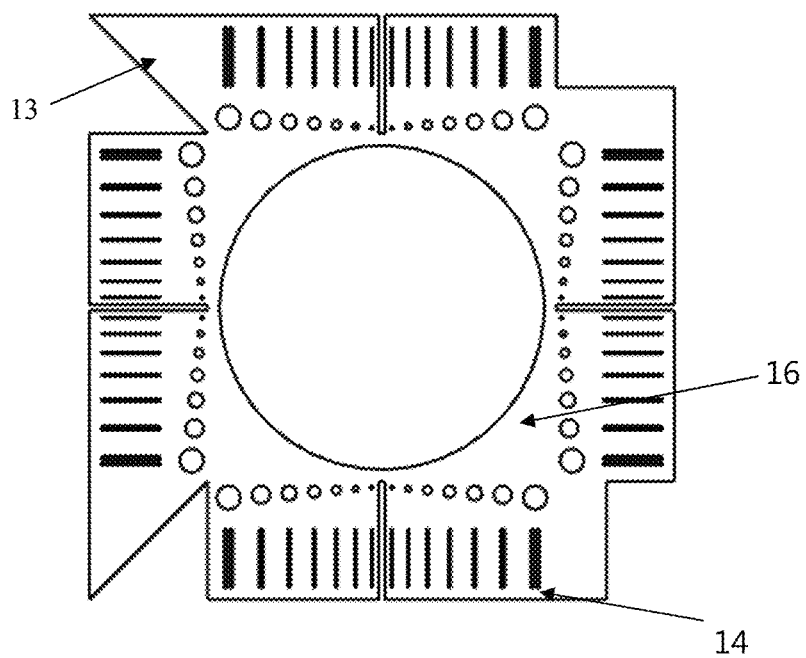
FIG. 3B is the front view of the embodiment of the test phantom set of the present invention.
Figure 4:
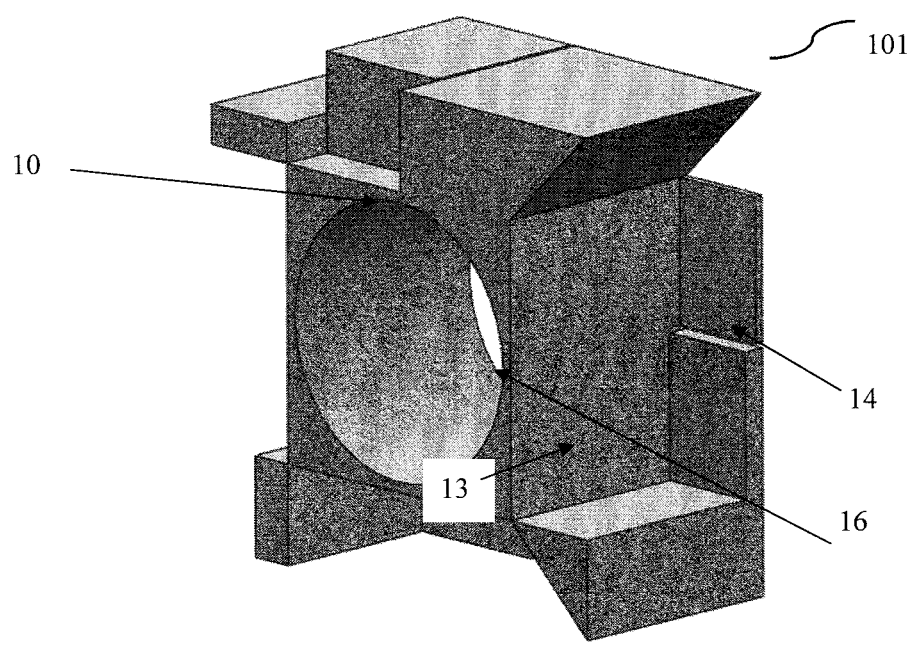
FIG. 4 is the rear stereogram of the embodiment of the test phantom set of the present invention.

As shown in FIGS. 3A, 3B and 4, in a preferred embodiment, the present invention is a test phantom set 101 that comprises eight groups of phantom fins 14, four groups of edge plates 13, one slot 16 and one stellated phantom 15. Specifically, there are circular grooves 12 with seven diameters and line pairs 11 with seven widths on the eight groups of phantom fins 14. The eight groups of phantom fins 14 have different thicknesses. Thus, different resolutions (frequency spectrum) under the same comparative (light intensity) can be compared, while different contrast values (degree of penetration) under the same resolution (spatial frequency) can also be obtained. The four edge phantoms 13 have the shapes enabling identification of direction, for example, the area difference is taken as the para-positional angle of the test phantom set 101.

Embodiment 1: Thickness Calculation Conducted when Aluminum is Adopted for the Phantom Fin Test phantoms in the present invention can be made of tungsten, aluminum or PMMA, and the thicknesses of phantom fins made of different materials need to be designed differently.

Figure 5:
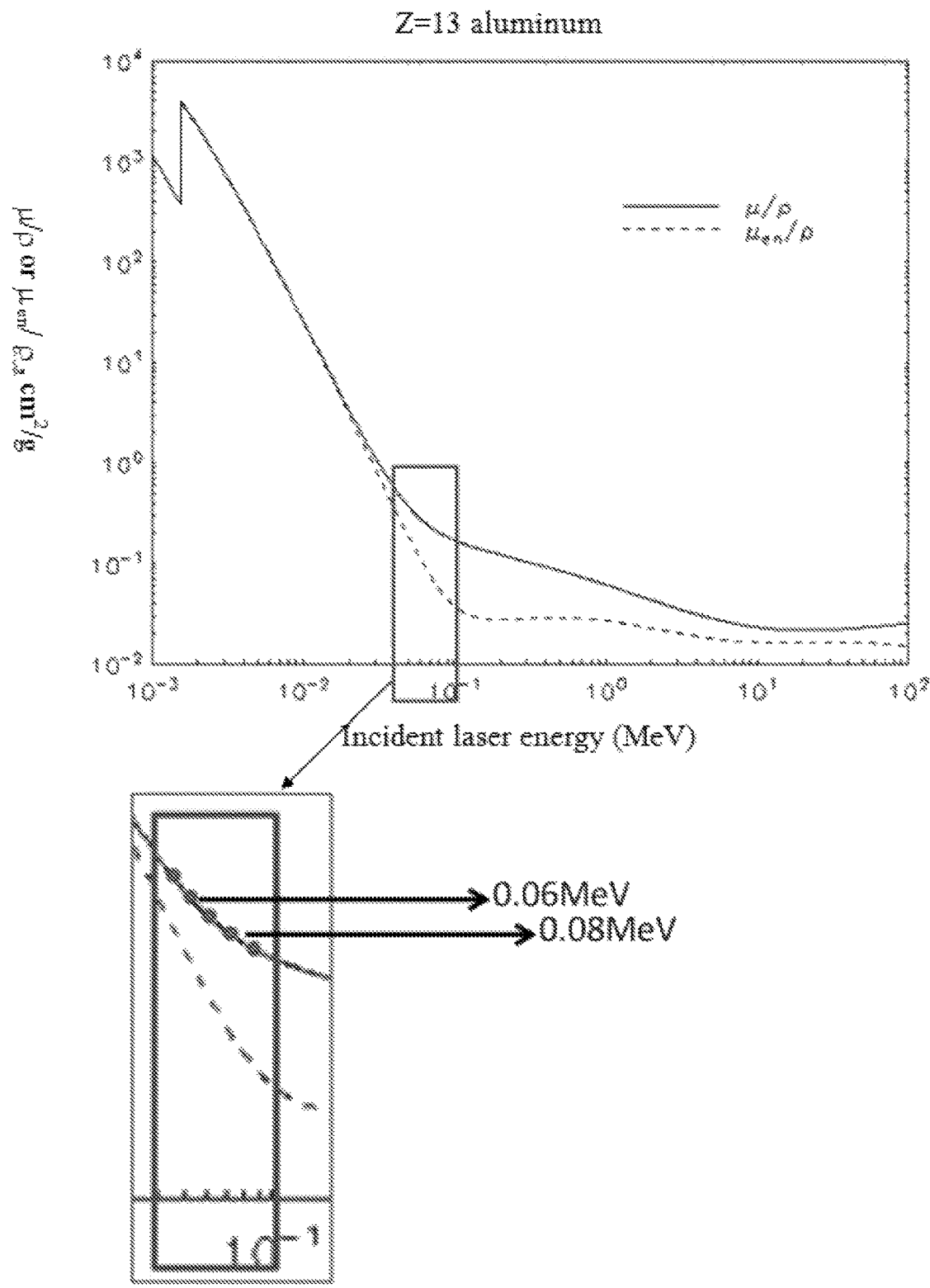
FIG. 5 is the calculated result of attenuation coefficient when aluminum is adopted for the phantom fin of the present invention.

Calculate the thickness of phantom fin (the optimal value of which is 70 kV and which can actually be 40 kV-100 kV) with the aluminum vs. 70 kV (7.00000E-02 MeV) X-ray energy attenuation factor by reference to FIG. 5, and the result is shown in Tables 1 and 2.

TABLE 1

Aluminum (Al) vs. Incident X-ray Energy Attenuation Factor
(Z = 13, Al density (p) = 2.7 g/cm$^3$)
($\mu$ = linear attenuation coefficient, $\mu_{en}$ = energy absorption coefficient)

| Incident laser energy Energy (MeV) | Mass attenuation coefficient $\mu/p$ (cm$^2$/g) | Mass energy absorption coefficient $\mu_{en}/p$ (cm$^2$/g) |
| --- | --- | --- |
| 4.00000E−02 | 5.685E−01 | 3.601E−01 |
| 5.00000E−02 | 3.681E−01 | 1.840E−01 |
| 6.00000E−02 | 2.778E−01 | 1.099E−01 |
| 8.00000E−02 | 2.018E−01 | 5.511E−02 |
| 1.00000E−01 | 1.704E−01 | 3.794E−02 |

Calculate the linear attenuation coefficient ($\mu$) in case of aluminum vs. incident X-ray energy 70 kV (7.00000E-02 MeV) with the interpolation method. Relevant details are set in below:

$$\frac{0.07 - 0.06}{0.08 - 0.06} = \frac{2.778 \times 10^{-1} - X}{2.778 \times 10^{-1} - 2.018 \times 10^{-1}}$$

Thus, X=2.398×10$^{-1}$ (1/cm). To sum up, it is known that when aluminum is under an incident X-ray energy 70 keV, the linear attenuation coefficient $\mu$ is 6.4746×10$^{-1}$ (1/cm)

Thickness (x) calculation method is set below:

$$I_x = I_0 e^{-\mu x}$$

-continued $$dI_x = -\mu I_x dx$$

$$\ln\left(\frac{I_x}{I_0}\right) = -\mu x$$

$$x = -\frac{\ln\left(\frac{I_x}{I_0}\right)}{\mu}$$

Figure 6:
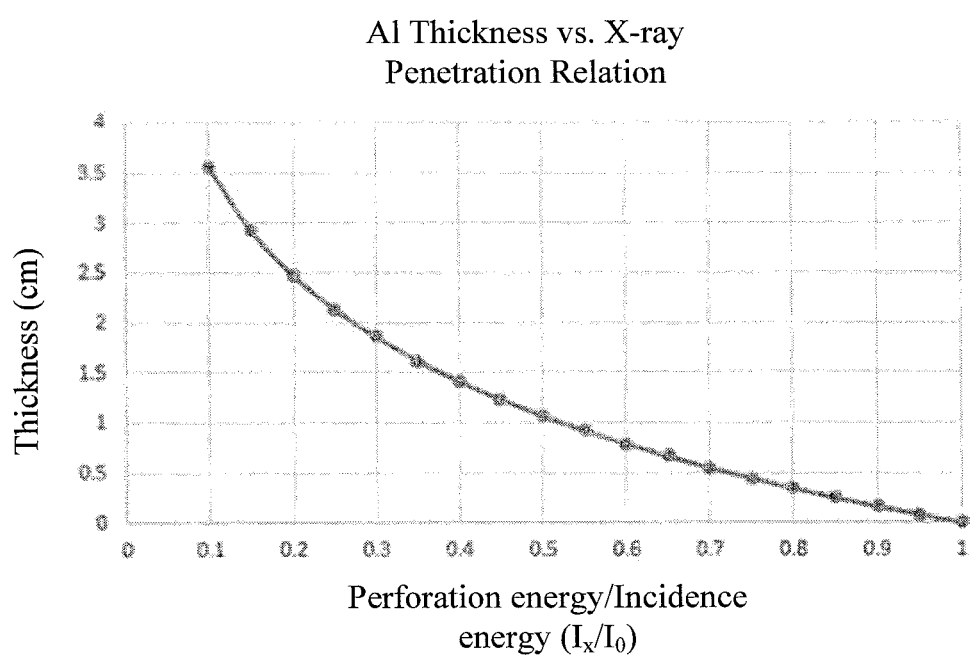
FIG. 6 is the calculated result of thickness when the phantom fin producing by aluminum of the present invention.

See FIG. 6. Table 2 can be obtained through said calculation, and the perforation energy/incidence energy ($I_x/I_0$) of 0.05, 0.25, 0.4, 0.5, 0.6, 0.75 and 0.9 are selected to calculate the thickness.

TABLE 2

Al Thickness vs. X-ray Penetration Relation

| Perforation energy/Incidence energy($I_x/I_0$) | Linear attenuation coefficient μ (1/cm) | Thickness x (cm) |
|---|---|---|
| 0.05 | 0.64746 | 4.6269 |
| 0.1 | 0.64746 | 3.5563 |
| 0.15 | 0.64746 | 2.9301 |
| 0.2 | 0.64746 | 2.48577 |
| 0.25 | 0.64746 | 2.1411 |
| 0.4 | 0.64746 | 1.4152 |
| 0.5 | 0.64746 | 1.0706 |
| 0.6 | 0.64746 | 0.789 |
| 0.75 | 0.64746 | 0.4443 |
| 0.9 | 0.64746 | 0.1627 |
| 0.95 | 0.64746 | 0.07922 |
| 1 | 0.64746 | 0 |

Embodiment 2: Measurement of Parameters of Test Phantom

Figure 7:
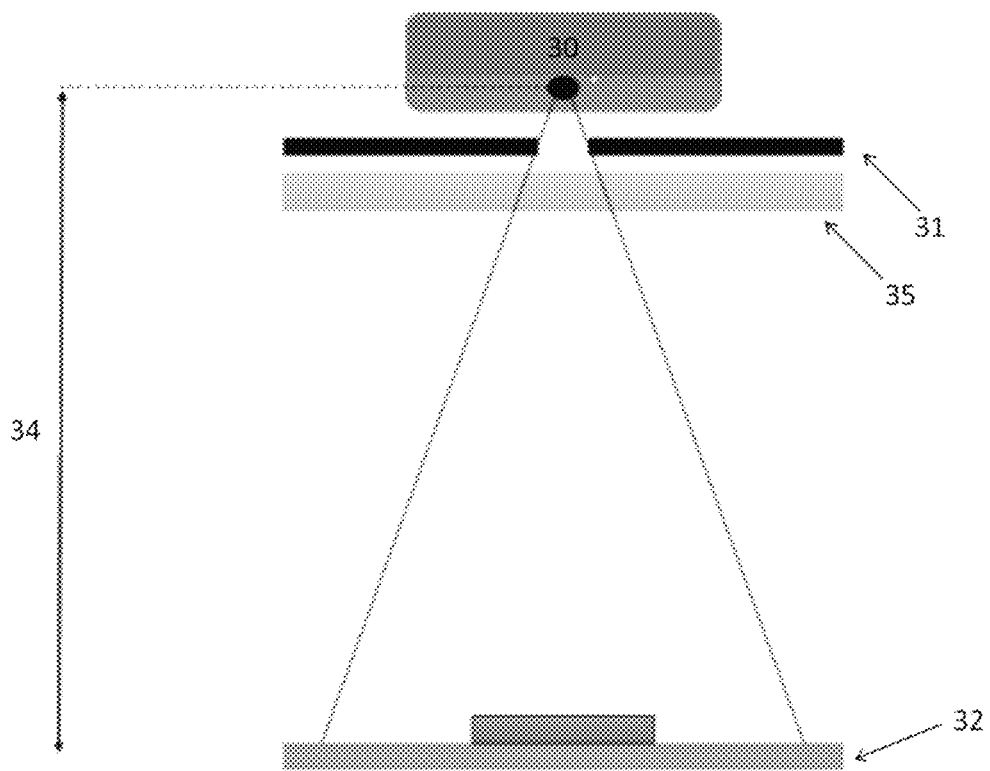
FIG. 7 is the lateral section view of the parameter measurement method of the present invention.
Figure 8:
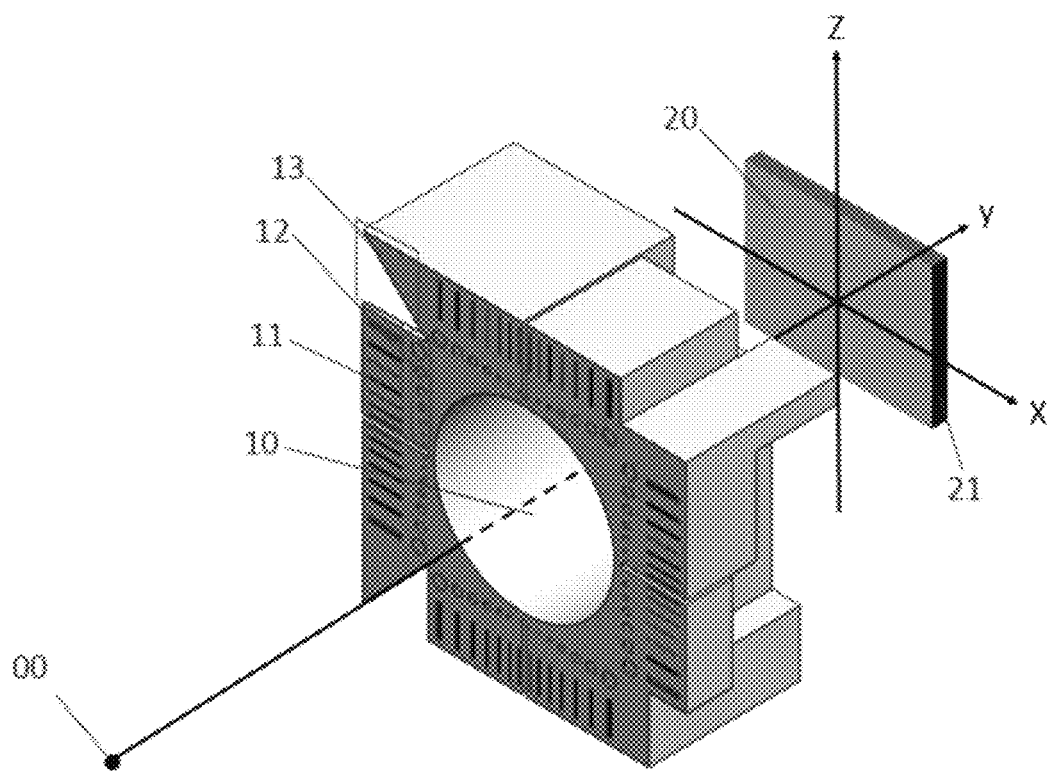
FIG. 8 is the configuration diagram of the test phantom set for the parameter measurement method of the present invention.

Referring to FIGS. 7 and 8, the test phantom set in the present invention needs to be matched with a set of X-ray imaging device, including one X-ray source and an image detector (namely an instrument able to measure the X-ray source); during measurement of parameter, attach the test phantom set to the front side of the image detector, make the rays of the X-ray source pass through the test phantom set, so that the image detector can receive, record and obtain an image; from the image, select the ultimate distinguishing degree and contrast ratio of a round slot or line pair of the test phantom; and take the value corresponding to the round slot or line pair as the maximum resolution of the X-ray imaging device.

The spatial frequency and spatial resolution represented by the line pairs and circular grooves on the phantom fin can be read macroscopically for judgment. In addition to the steps of said measurement method, further measurements of MTF, NPS and DOE can be obtained by the edge plate in the present invention.

Select any edge plate of the test phantoms set, obtain the ESF (edge spread function) after accessing the image with the image detector, and get the LSF through differential calculation. The computational formula is set in below:

$$LSF(x) = \frac{dESF(x)}{dx}$$

Figure 9:
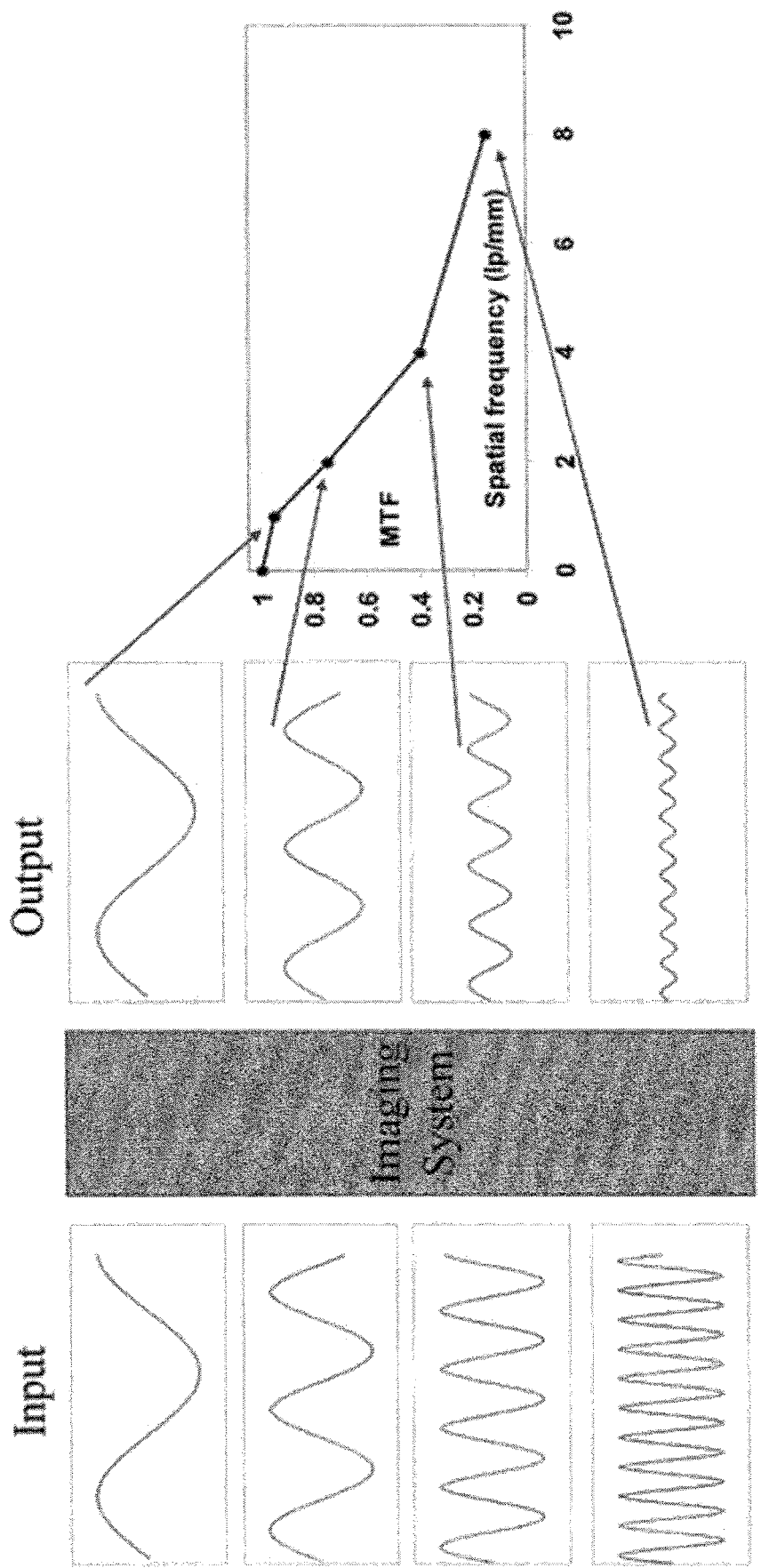
FIG. 9 is the diagram for the modulation transfer function (MTF) corresponding to the spatial frequency of line pairs of the present invention.

Referring to FIG. 9, the distribution of spatial pixel strengths of all circular grooves can correspond to LSFs respectively; besides, the MTF can be obtained through Fourier transformation. The computational formula is set in below:

$$MTF(x) = FT\{LSF(x)\}$$

Figure 10:
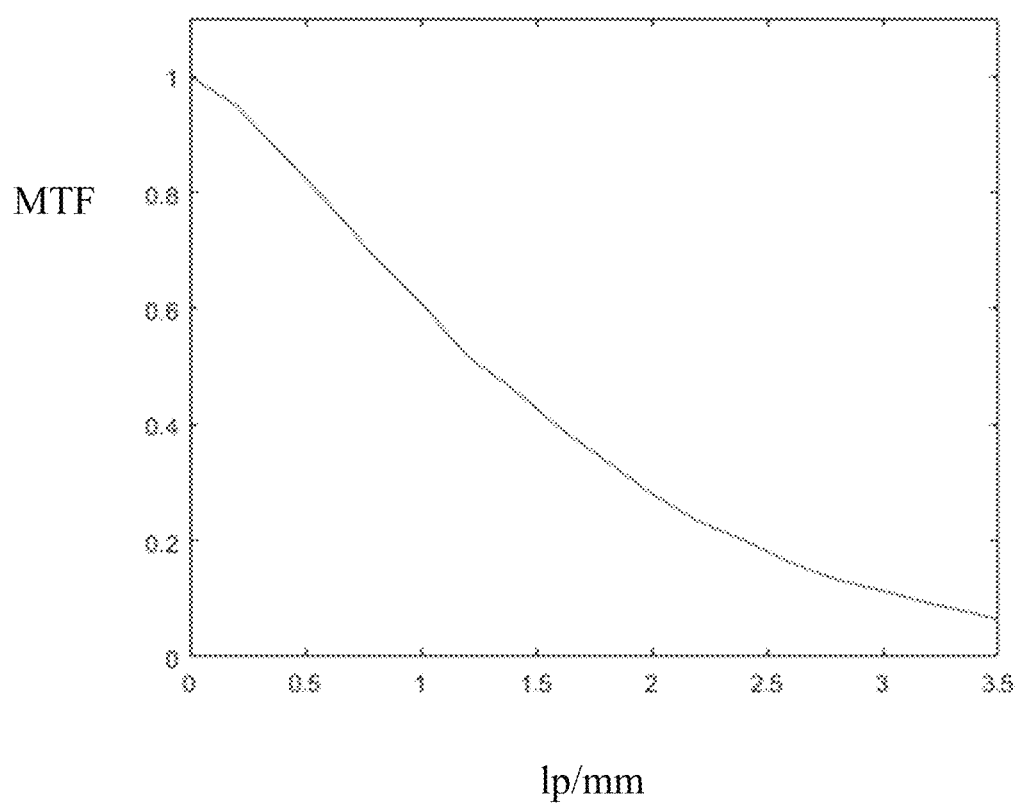
FIG. 10 is the calculated result diagram of the modulation transfer function (MTF) formed for the phantom fin of the present invention.

Referring to FIGS. 9 and 10, spatial frequencies of all line pairs can correspond to MTFs respectively.

Figure 11:
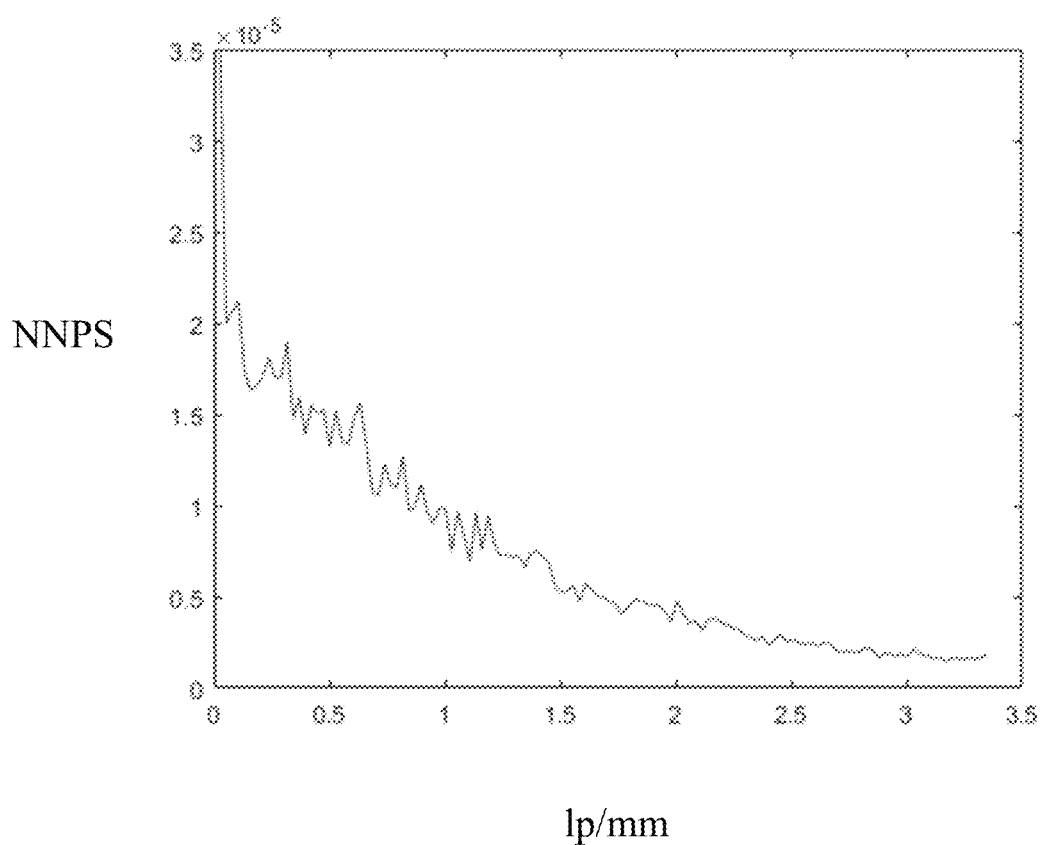
FIG. 11 is the calculated result diagram of the noise power spectrum (NPS) for the phantom fin of the present invention.

Then, referring to FIG. 11, the data can be measured and obtained otherwise based on the international standard IEC 62220-1-1, so that one input power ($W_{in}$) and one output power ($W_{out}$) of the image detector can be obtained, and the NPS can be calculated. The computational formulas are set in below respectively:

$$W_{in}(u, v) = K_a \cdot SNR_{in}^2$$

$$W_{out}(u_n, v_k) = \frac{\Delta x \Delta y}{M \cdot \text{matrix size}} \sum_{m=1}^{M} \left| \sum_{i=1}^{\text{matrix size}} \sum_{j=1}^{\text{matrix size}} [I(x_i, y_j) - S(x_i, y_j)] \exp[-2\pi i(u_n x_i + v_k y_j)] \right|^2$$

Figure 12:
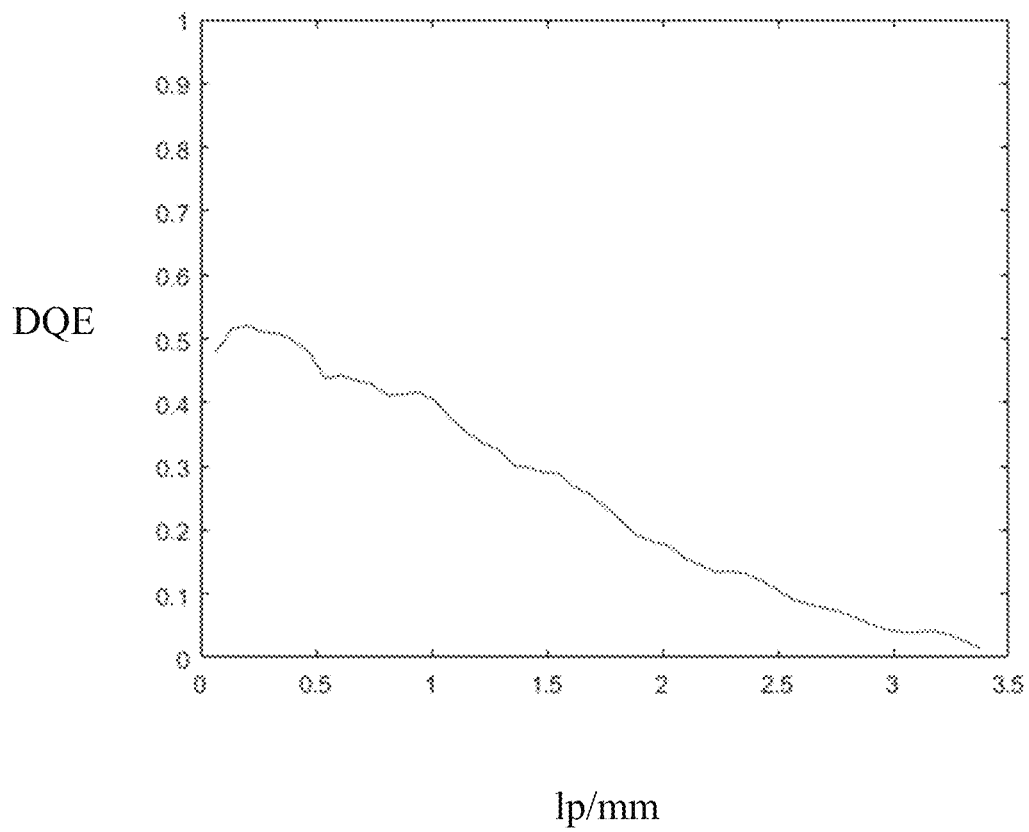
FIG. 12 is the calculated result diagram of the detective quantum efficiency (DQE) for the phantom fin of the present invention.

Referring to FIG. 12, the DQE can be calculated based on said parameters. The computational formulas are set in below respectively $$DQE(u, v) = MTF^2(u, v) \frac{W_{in}(u, v)}{W_{out(u,v)}}$$

Embodiment 3: Measurement of Focal Spot of Test Phantom

Figure 13A:
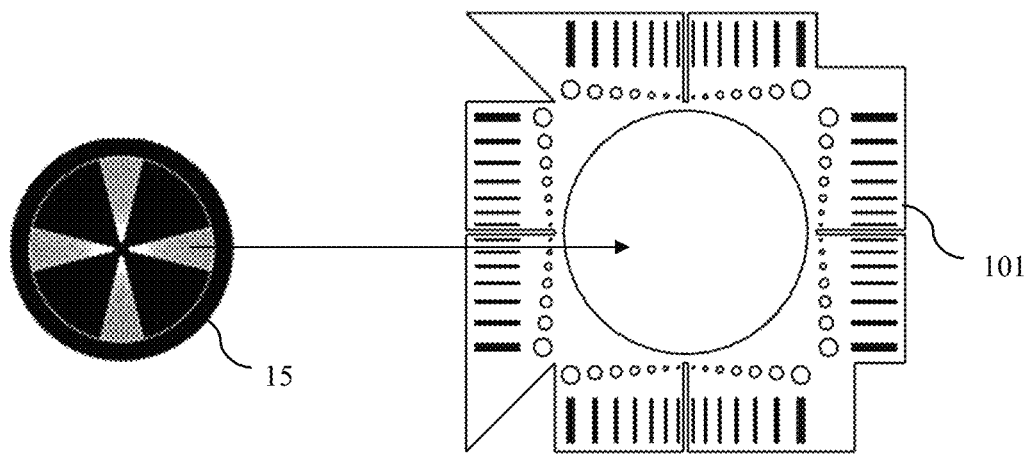
FIG. 13A and FIG. 13B is the diagram of the connection between the test phantom sets and the stellated phantom in the present invention.
Figure 13B:
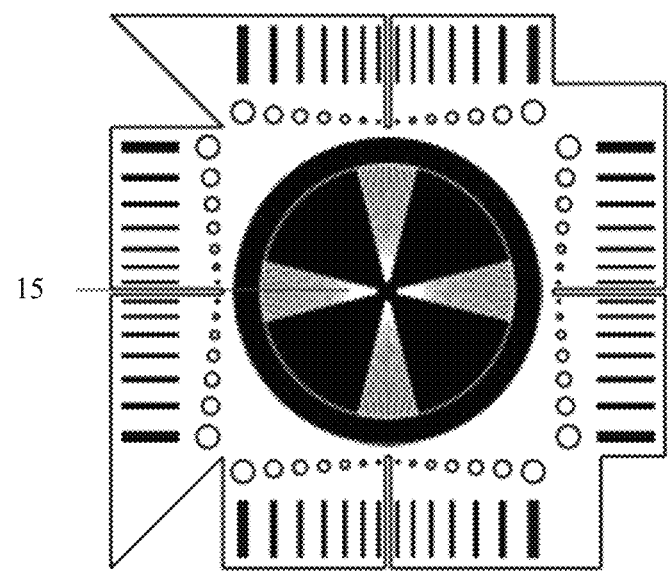

As shown in FIGS. 13A and 13B, in the test phantom set 101, the slot body 16 has a circular hollow groove 10, and these test phantoms 100 are connected to the periphery of the slot 16. Specifically, stellated phantom 15 is placed in the circle hollow slot 10 to increase the functions of measuring focal spot, extreme resolution and defocusing value; it is preferred that based on the stock size of stellated phantom, the diameter dimension of circular hollow groove 10 is about 55 mm.

Figure 14:
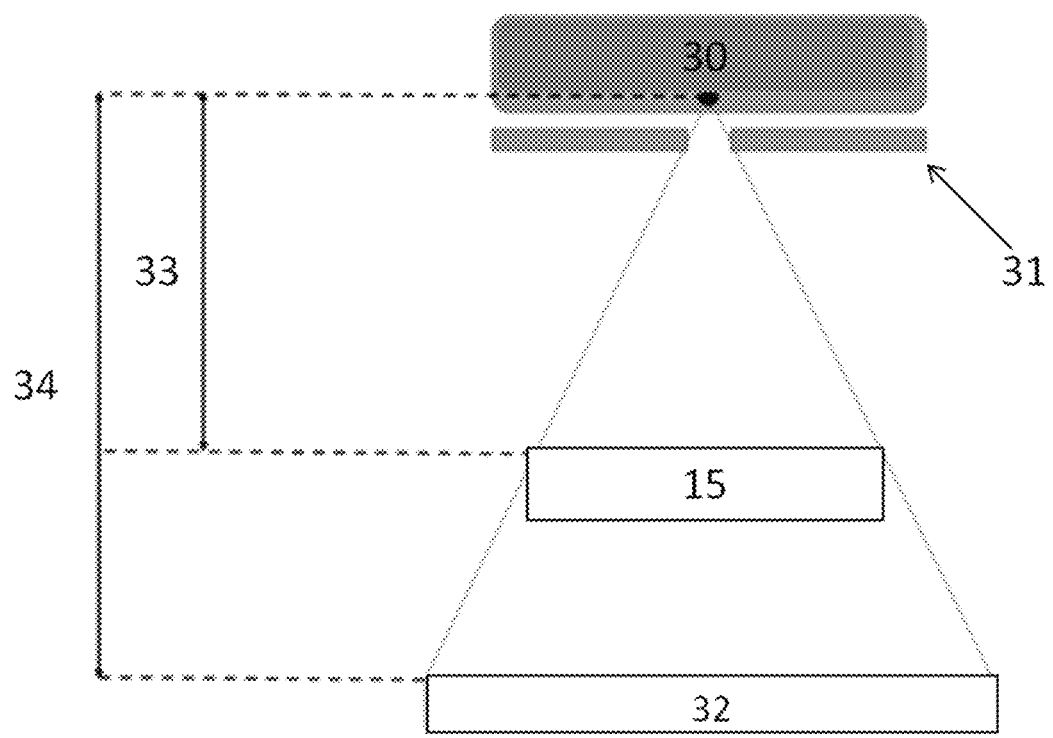
FIG. 14 is the lateral section view of focal spot measurement method of the present invention, including the placement position during measurement of combination of test phantoms.

Referring to FIG. 14, said combination of test phantoms with stellated phantom is placed between the X-ray source 00 and the image detector 32 during measurement of focal spot 30. It is preferred that the distance from the X-ray source to the image detector (SID) is 1.3 to 2 times of the distance from the X-ray source to the test phantom set (SOD) (M=SID/SOD=1.3~2). Specifically, the X-ray source, the test phantom set and the image detector have a distance ratio, the rays of the X-ray source are made to pass through the test phantom set, so that the image detector can receive, record and obtain an image; from the image, the ultimate distinguishing degree and contrast ratio of an interval of the stellated phantom are selected; and the diameter values of the distance ratio and the interval to obtain a focal spot dimension or value.

To sum up, the phantom system of the present invention integrates most functions of mass parameters of X-ray system that can be obtained by measurement or calculation, measure multiple parameters at one time and solve an issue in the prior art that a stellated phantom can only be used independently.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

The invention claimed is:

1. A test phantom set for X-ray imaging, which comprises:
a circular hollow groove provided for penetrating through a slot body, and
a plurality of test phantoms configured to a periphery of the slot body,
wherein the plurality of test phantoms further comprise:
a phantom fin, having a plurality of circular grooves and a plurality of line pairs;
an edge plate configured to one side of the phantom fin, and
a phantom configured to be placed in the circular hollow groove.

2. The test phantom set defined in claim 1, wherein the circular grooves have diameters of 0.5 mm~4 mm.

3. The test phantom set defined in claim 1, wherein the line pairs have widths of 1 line pairs per mm (1 p/mm)~10 line pairs per mm (1 p/mm).

4. The test phantom set defined in claim 1, comprising a plurality of phantom fins, wherein each of the phantom fins has different thickness.

5. The test phantom set defined in claim 1, wherein the phantom fin has a thickness of 0.16 mm~4.63 mm.

6. The test phantom set defined in claim 1, wherein the phantom fin and the edge plate are made of tungsten, aluminum or PMMA.

7. The test phantom set defined in claim 1,
wherein each of test phantoms has a plurality of phantom fins and an edge plate;
wherein each of the edge plates is configured to have a shape enabling an identification of a direction by different areas of the edge plates provided for para-positional angle of the test phantom set.

8. The test phantom set defined in claim 7, comprising: a stellated phantom being placed in the circular hollow groove; wherein the test phantoms are attached to the periphery of the slot body.

9. The test phantom set defined in claim 8, wherein the circular hollow groove has a diameter of 50 mm to 55 mm.

10. The test phantom set defined in claim 8, wherein the slot body is made of tungsten, aluminum or PMMA.

11. A measurement method for the focal spot of a test phantom for X-ray imaging, comprising:
(a) providing an X-ray imaging device comprising an X-ray source and an image detector;
(b) placing a test phantom set defined in claim 8 between the X-ray source and the image detector, wherein a distance ratio of a distance from the X-ray source to the image detector to a distance from the X-ray source to the test phantom set is 1 to 3;
(c) irradiating X-rays from the X-ray source passing through a stellated phantom of the test phantom set, then received by the image detector to record and obtain an image;
(d) from the image, selecting one region with a limitation distinguishing degree or a limitation contrast ratio of the stellated phantom; and
(e) calculating the diameter and angle value of the region and the distance ratio to obtain a focal spot size or a focal spot value.

12. A measurement method for the parameters of a test phantom for X-ray imaging, comprising:
(a) providing an X-ray imaging device comprising an X-ray source and an image detector;
(b) placing a test phantom set defined in claim 7 in a front side of the image detector;
(c) irradiating X-rays from the X-ray source passing through the test phantom set, then received by the image detector to record and obtain an image;
(d) from the image, selecting one round slot with a limitation distinguishing degree or one line pair with a limitation contrast ratio of the test phantom set; and
(e) taking a value corresponding to the round slot or the line pair as a maximum resolution of the X-ray imaging device.

13. The method defined in claim 12, further comprising:
(f) from the image, selecting one edge plate of the test phantom set to obtain an edge spread function (ESF); and
(g) calculating the differential of the ESF to obtain a line spread function.

14. The method defined in claim 13, further comprising:
(h) calculating a Fourier transformation of the line spread function to obtain a modulation transfer function (MTF).

15. The method defined in claim 14, further comprising:
(i) calculating the MTF based on a standard criterion to obtain an input power ($W_{in}$) and an output power ($W_{out}$) of the image detector; and
(g) calculating the MTF, output power and input power to obtain a detective quantum efficiency.

* * * * *